United States Patent [19]

Kaltenbach, III

[11] Patent Number: 5,880,295
[45] Date of Patent: Mar. 9, 1999

[54] PROCESS FOR THE PREPARATION OF DIAMINE INTERMEDIATES USEFUL IN THE SYNTHESIS OF HIV PROTEASE INHIBITORS

[75] Inventor: Robert Frank Kaltenbach, III, New Castle, Del.

[73] Assignee: DuPont Pharmaceuticals Company, Wilmington, Del.

[21] Appl. No.: 666,032

[22] Filed: Jun. 19, 1996

Related U.S. Application Data

[60] Division of Ser. No. 268,609, Jun. 30, 1994, Pat. No. 5,559,252, which is a continuation-in-part of Ser. No. 197,630, Feb. 16, 1994, Pat. No. 5,610,294.

[51] Int. Cl.$^6$ ..................... C07D 317/28; C07D 317/34
[52] U.S. Cl. ............................. 549/450; 549/451
[58] Field of Search ..................... 549/450, 451

[56] References Cited

U.S. PATENT DOCUMENTS 5,294,720  3/1994  Jadhav et al. ........................... 546/265

FOREIGN PATENT DOCUMENTS 402646  12/1990  European Pat. Off. .
WO9323361  11/1993  WIPO .

OTHER PUBLICATIONS

W. R. Baker and S. L. Condon, J. Org. Chem., 1993, 58, 3277–3284.

D. J. Kempf et al., J. Org. Chem., 1992, 57, 5692–5700.

Lam et al., Science, 1994, 263, 380–384.

B. Chenera, J.C. Boehm & G. B. Dreyer, Bioorganic & Med. Chem. Lett., 1991, 1, 219–222.

P. K. Jadhav & F. J. Woerner, Bioorganic & Med. Chem. Lett., 1992, 2, 353–356.

A. K. Ghosh, S. P. McKee & W. J. Thompson, Tetrahedron Lett., 1991, 32, 5729–5732.

G. B. Dreyer et al., Biochemistry 1993, 32, 937–947.

Kappes, E. et al *J. Carbohydrate Chem.* 8, 371–378 (1989).

Inouye, S. et al *Tetrahedron* 24, 2125–2144 (1968).

*Primary Examiner*—Richard L. Raymond
*Attorney, Agent, or Firm*—Blair Q. Ferguson

[57] ABSTRACT

The present invention provides a process for the preparation of compounds of formula (V) below, and analogs thereof, which are useful as intermediates for the synthesis of HIV protease inhibitors, including cyclic ureas.

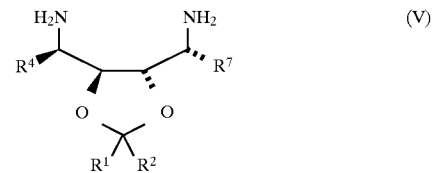

14 Claims, No Drawings

PROCESS FOR THE PREPARATION OF DIAMINE INTERMEDIATES USEFUL IN THE SYNTHESIS OF HIV PROTEASE INHIBITORS

This is a division of application Ser. No. 08/268,609, filed Jun. 30, 1994, now U.S. Pat. No. 5,559,252, which is a continuation-in-part of U.S. patent application Ser. No. 08/197,630 filed Feb. 16, 1994, now U.S. Pat. No. 5,610,294. The disclosure of this earlier filed application is hereby incorporated herein by reference.

FIELD OF THE INVENTION

This invention relates to compounds which are useful as intermediates for the synthesis of human immunodeficiency virus (HIV) protease inhibitors, including cyclic carbonyls. This invention also relates to methods for the synthesis of HIV protease inhibitors, including cyclic carbonyls.

BACKGROUND OF THE INVENTION

Many nonpeptide C-2 symmetric and pseudosymmetric compounds have shown good biological activity as human immunodeficiency virus (HIV) protease inhibitors. Compounds and methods for their preparation are increasingly found in the literature. (Kempf et al., *J. Org. Chem.* 57, 5692–5700 (1992); Livermore et al., *J. Med. Chem.* 36, 3784–3794 (1993); Lam et al., *Science* 263, 380–384 (1994); Jadhav et al., WO 93/07128; EP 402,646; Dreyer et al., *Biochemistry* 32, 937–47 (1993); Sowin et al. WO 93/23361; Jadhav et al., *Bioorganic & Med. Chem. Lett.* 2, 353–356 (1992); Jadhav et al., U.S. Pat. No. 5,294,720.

U.S. Pat. No. 5,294,720 and European Patent Application 402,646 A1 describe the synthesis of diamine

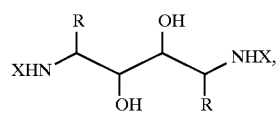

via coupling of aldehydes derived from suitably protected aminoacids.

Baker and Condon, *J. Org. Chem.* 1993, 58, 3277–3284, disclose a method for the preparation of linear diaminodiols from (−)-2,3-isopropylidene-D-threitol shown below.

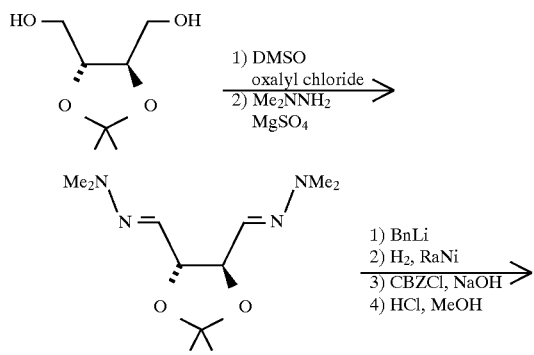

European Patent Application 402,646 A1 also describes the synthesis of bisoxime (C) from the bisamide (B). This product was obtained in relatively poor yields and no further transformations were disclosed.

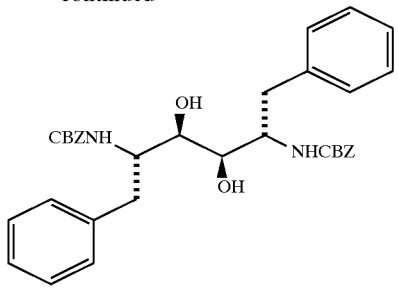

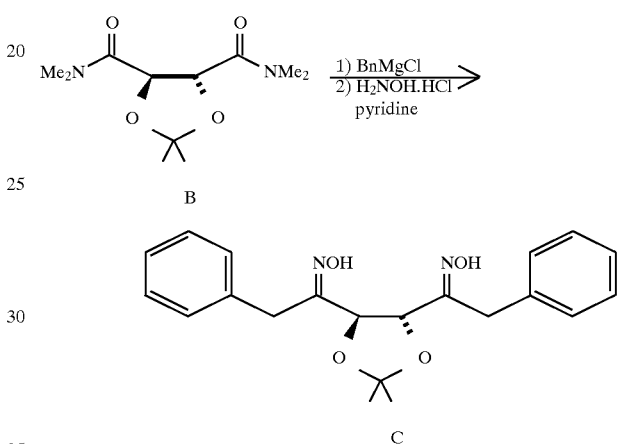

Lam et al., PCT International Publication Number WO 93/07,128 discloses cyclic carbonyl compounds and derivatives thereof which are useful as human immunodeficiency virus (HIV) protease inhibitors for the treatment of HIV infection. The compounds disclosed in WO 93/07128 include cyclic HIV protease inhibitor compounds of the formula below where W may be —N($R^{22}$)C(=O)N($R^{23}$)—.

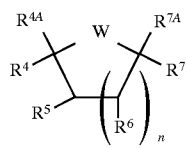

The above methods for the preparation of linear diaminodiols use relatively expensive starting materials and toxic reagents.

The present invention provides a improved synthetic processes for the preparation of diamine intermediates useful for the synthesis of HIV protease inhibitors. The process of the present inventions uses inexpensive chiral raw materials and environmentally nonhazardous reagents.

None of the above-cited references describe the methods of the present invention for the synthesis of diamines useful as intermediates for the synthesis of HIV protease inhibitors.

SUMMARY OF THE INVENTION

The present invention provides a process for the preparation of compounds of formula (V) below, which are useful as intermediates for the synthesis of HIV protease inhibitors, including cyclic ureas.

The present invention provides a process for the preparation of compounds of formula (V):

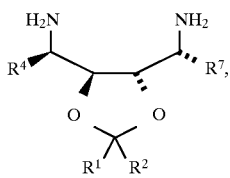

or intermediates for the synthesis of compounds of formula (V), wherein $R^4$, $R^7$, $R^1$ and $R^2$ are defined below, said process comprising one or more of the following steps:

(1) contacting a compound of formula (I):

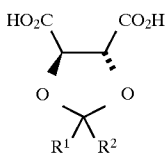

in an aprotic solvent with a carboxyl activating agent, followed by reaction with a N,O-dialkylhydroxylamine of formula $R^6NHOR^5$, to form a compound of formula (II):

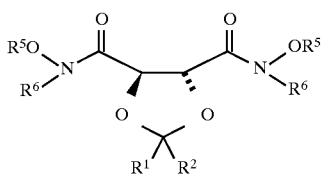

wherein $R^1$, $R^2$, $R^5$, and $R^6$ are defined below;

(2) contacting a compound of formula (II) in an aprotic solvent with a nucleophilic organometallic reagent being suitable for the addition of a $R^4$- or $R^7$-substituent to amides of the structure of compound (II), thereby to form a compound of formula (III):

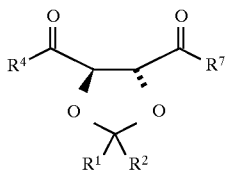

wherein $R^1$, $R^2$, $R^4$ and $R^7$ are defined below;

(3) reacting a compound of formula (III) in a protic solvent with a hydroxylamine of formula $NH_2OR^3$, to form a compound of formula (IV):

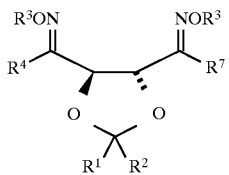

wherein $R^1$, $R^2$, $R^4$, $R^7$, and $R^3$ are defined below;

(4) contacting a compound of formula (IV) with a reducing agent to effect the conversion of the oxime groups in the compound of formula (IV) to amine groups, to obtain a compound of formula (V).

DETAILED DESCRIPTION OF THE INVENTION

There is provided by this invention a process for preparation of compounds of formula (V):

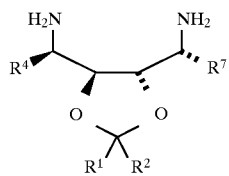

or intermediates for the synthesis of compounds of formula (V), said compounds being useful as intermediates for the preparation of HIV protease inhibitors, including cyclic urea HIV protease inhibitors, wherein:

$R^1$ and $R^2$ are independently: H, $C_1$–$C_4$ alkyl, $C_1$–$C_4$ alkoxy, $C_6$–$C_{10}$ aryl, $C_7$–$C_{14}$ arylalkyl, $C_1$–$C_4$ haloalkyl, $C_3$–$C_7$ cycloalkyl, or can be taken together to be keto;

alternatively, $R^1$ and $R^2$ can be taken together with the carbon to which they are attached to form a 3–7 membered saturated carbocyclic ring system;

$R^4$ and $R^7$ are independently:

$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or 0–3 $R^{12}$;
a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ is selected from one or more of the following:

H, keto, halogen, cyano, —$CH_2NR^{13}R^{14}$, —$NR^{13}R^{14}$, —$OR^{13}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, 2-(1-morpholino)ethoxy, or azido;
$C_3$–$C_{10}$ cycloalkyl substituted with 0–2 $R^{12}$;
$C_1$–$C_4$ alkyl substitued with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$;
a $C_5$–$C_{14}$ carbocyclic residue substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is:

H, halogen, cyano, —$CH_2N(R^{13A})R(^{14A})$, —$N(R^{13A})R(^{14A})$, —OH, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, 2-(1-morpholino)ethoxy, azido, aryl($C_1$–$C_3$ alkyl), a $C_5$–$C_{14}$ carbocyclic residue; or
a 5- to 10-membered heterocyclic ring system containing 1 to 4 heteroatoms independently selected from oxygen, nitrogen or sulfur, said heterocyclic ring system substituted with 0–3 $R^{12A}$.

$R^{12}$, when a substituent on carbon, is:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene, $C_1$–$C_4$ hydroxyalkyl, methylenedioxy, ethylenedioxy, $C_1$–$C_4$ haloalkyl, $C_1$–$C_4$ haloalkoxy, 2-(1-morpholino)ethoxy, or
  a 5- or 6-membered heterocyclic ring containing from 1 to 4 heteroatoms independently selected from oxygen, nitrogen or sulfur;
  or $R^{12}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, —$NR^{13}R^{14}$;

$R^{12}$, when a substituent on nitrogen, is:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl;

$R^{12A}$, when a substituent on carbon, is:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13a}$, $C_1$–$C_4$ alkyl substituted with —$NH_2$, —$NH_2$, —$NHMe$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, 2-(1-morpholino)ethoxy,
  a 5- or 6-membered heterocyclic ring containing from 1 to 4 heteroatoms independently selected from oxygen, nitrogen or sulfur;
  or $R^{12A}$ may be a 3- or 4-carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NH_2$;

$R^{12A}$, when a substituent on nitrogen, is:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, or $C_1$–$C_4$ haloalkyl;

$R^{13}$ is selected from:
  H;
  phenyl substituted with 0–3 $R^{11A}$;
  benzyl substituted with 0–3 $R^{11A}$;
  $C_1$–$C_6$ alkyl substituted with 0–3 $R^{11A}$;
  $C_2$–$C_4$ alkenyl substituted with 0–3 $R^{11A}$;
  $C_3$–$C_6$ alkoxyalkyl substituted with 0–3 $R^{11A}$;
  an amine protecting group when $R^{13}$ is bonded to N;
  a hydroxy protecting group when $R^{13}$ is bonded to O;

$R^{14}$ is selected from: hydrogen; hydroxy; $C_1$–$C_6$ alkoxy; $C_2$–$C_6$ alkenyl; phenyl; benzyl; an amine protecting group when $R^{14}$ is bonded to N; a hydroxy protecting group when $R^{14}$ is bonded to O; or $C_1$–$C_6$ alkyl substituted with 0–3 groups selected from OH, $C_1$–$C_4$ alkoxy, halogen, $NH_2$, —$NH(C_1$–$C_4$ alkyl);

$R^{13}$ and $R^{14}$ can alternatively join to form —$(CH_2)_4$-, —$(CH_2)_5$-, —$CH_2CH_2N(R^{15})CH_2CH_2$—, or —$CH_2CH_2OCH_2CH_2$—;

$R^{13A}$ and $R^{14A}$ are independently selected from: H, $C_1$–$C_6$ alkyl;

$R^{13A}$ and $R^{14A}$ can alternatively join to form —$(CH_2)_4$-, —$(CH_2)_5$-, —$CH_2CH_2N(R^{15})CH_2CH_2$—, or —$CH_2CH_2OCH_2CH_2$—;

$R^{15}$ is H or $CH_3$;

m is 0, 1 or 2;

said process comprising one or more of the following steps:

step (1) (amide formation): (a) contacting a compound of formula (I):

$$\text{HO}_2\text{C} \diagdown \diagup \text{CO}_2\text{H} \quad \text{(I)}$$
$$\text{O} \quad \text{O}$$
$$R^1 \quad R^2$$

in an aprotic solvent with a carboxyl activating agent, followed by; (b) addition of of a N,O-dialkylhydroxylamine of formula $R^6NHOR^5$, to form a compound of formula (II):

$$R^5O\diagdown N \diagdown \diagup N \diagup OR^5 \quad \text{(II)}$$
$$R^6 \quad \quad \quad R^6$$
$$O \quad O$$
$$R^1 \quad R^2$$

wherein $R^1$ and $R^2$ are defined as above and $R^5$ and $R^6$ are independently $C_1$–$C_4$ alkyl or benzyl;

step (2) (ketone formation): contacting a compound of formula (II) in an aprotic solvent with a nucleophilic organometallic reagent, said nucleophilic organometallic reagent being suitable for the addition of a $R^4$- or $R^7$-substituent to amides of the structure of compound (II), to form a compound of formula (III):

$$R^4 \diagdown \diagup R^7 \quad \text{(III)}$$
$$O \quad O$$
$$R^1 \quad R^2$$

wherein $R^1$, $R^2$, $R^4$ and $R^7$ are defined as above;

step (3) (oxime formation): reacting a compound of formula (III) in a protic solvent with an hydroxylamine of formula $NH_2OR^3$, to form a compound of formula (IV):

$$R^3ON \diagdown \diagup NOR^3 \quad \text{(IV)}$$
$$R^4 \quad \quad R^7$$
$$O \quad O$$
$$R^1 \quad R^2$$

wherein $R^1$, $R^2$, $R^4$ and $R^7$ are defined as above and $R^3$ is hydrogen, $C_1$–$C_6$ alkyl, benzyl, arylcarbonyl or ($C_1$–$C_6$ alkyl)carbonyl;

step (4) (amine formation): contacting a compound of formula (IV) in a suitable solvent with a reducing agent to effect the conversion of the oxime groups in the compound of formula (IV) to amine groups, to obtain a compound of formula (V).

The present invention includes a process for the preparation of compounds of formula (IV):

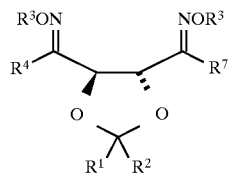

said process comprising one or more of the following steps:

step (1) (amide formation): (a) contacting a compound of formula (I):

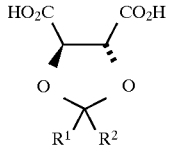

in an aprotic solvent with a carboxyl activating agent, followed by; (b) addition of a N,O-dialkylhydroxylamine of formula $R^6NHOR^5$, to form a compound of formula (II)

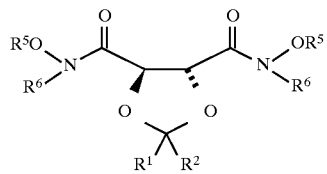

wherein $R^1$ and $R^2$ are defined as above and $R^5$ and $R^6$ are independently $C_1$–$C_4$ alkyl or benzyl;

step (2) (ketone formation): contacting a compound of formula (II) in an aprotic solvent with a nucleophilic organometallic reagent, said nucleophilic organometallic reagent being suitable for the addition of a $R^4$- or $R^7$-substituent to amides of the structure of compound (II), to form a compound of formula (III):

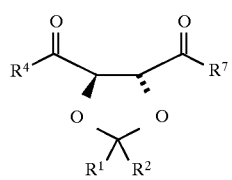

wherein $R^1$, $R^2$, $R^4$ and $R^7$ are defined as above;

step (3) (oxime formation): reacting a compound of formula (III) in a protic solvent with an hydroxylamine of formula $NH_2OR^3$, to form a compound of formula (IV):

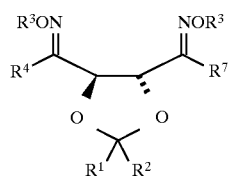

wherein $R^1$, $R^2$, $R^4$ and $R^7$ are defined as above and $R^3$ is hydrogen, $C_1$–$C_6$ alkyl, benzyl, arylcarbonyl or ($C_1$–$C_6$ alkyl)carbonyl.

The present invention also provides a process for the preparation of compounds of formula (III):

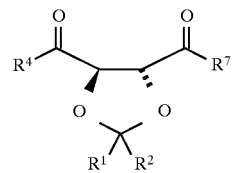

said process comprising one or more of the following steps:

step (1) (amide formation): (a) contacting a compound of formula (I):

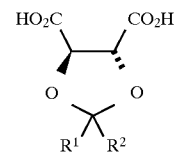

in an aprotic solvent with a carboxyl activating agent, followed by; (b) addition of a N,O-dialkylhydroxylamine of formula $R^6NHOR^5$, to form a compound of formula (II):

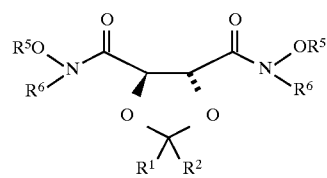

wherein $R^1$ and $R^2$ are defined as above and $R^5$ and $R^6$ are independently $C_1$–$C_4$ alkyl or benzyl;

step (2) (ketone formation): contacting a compound of formula (II) in an aprotic solvent with a nucleophilic organometallic reagent, said nucleophilic organometallic reagent being suitable for the addition of a $R^4$- or $R^7$-substituent to amides of the structure of compound (II), to form a compound of formula (III):

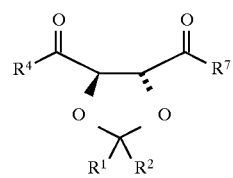

wherein $R^1$, $R^2$, $R^4$ and $R^7$ are defined as above.

There is also provided by this invention a process for the preparation of compounds of formula (II):

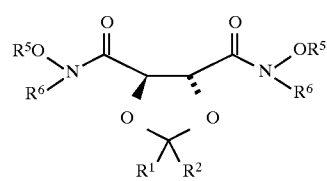

said process comprising the step of:

step (1) (amide formation): (a) contacting a compound of formula (I):

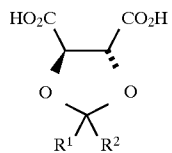

in an aprotic solvent with a carboxyl activating agent, followed by; (b) addition of a N,O-dialkylhydroxylamine of formula $R^6NHOR^5$, to form a compound of formula (II):

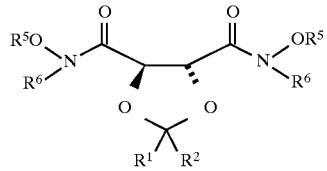

wherein $R^1$ and $R^2$ are defined as above and $R^5$ and $R^6$ are independently $C_1$–$C_4$ alkyl or benzyl.

Preferred in the present invention is a process as described above wherein:

$R^1$ and $R^2$ are methyl, ethyl, or can be taken together with the carbon to which they are attached to form cyclopentyl;

$R^4$ and $R^7$ are $C_1$–$C_8$ alkyl substituted with 0–1 $R^{11}$;

$R^{11}$ is

H; halogen; —$OR^{13}$;

$C_3$–$C_{10}$ cycloalkyl substituted with 0–2 $R^{12}$;

aryl substituted with 0–2 $R^{12}$; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{12}$, when a substituent on carbon, is selected from one or more of the following:

benzyloxy, halogen, methyl, $C_1$–$C_4$ alkoxy, $CF_3$, 2-(1-morpholino)ethoxy, cyano, $C_3$–$C_6$ cycloalkoxy, $C_1$–$C_4$ alkyl substituted with —$NR^{13}R^{14}$, —$NR^{13}R^{14}$;

$R^{12}$, when a substituent on nitrogen, is methyl;

$R^{13}$ is H, $C_1$–$C_4$ alkyl, $C_2$–$C_4$ alkenyl, or benzyl;

$R^{14}$ is H, $CF_3$, $C_1$–$C_4$ alkyl, $C_1$–$C_4$ alkoxy, $C_2$–$C_4$ alkenyl, or benzyl;

$R^{13}$ and $R^{14}$ can alternatively join to form —$(CH_2)_4$-, —$(CH_2)_5$-, —$CH_2CH_2N(R^{15})CH_2CH_2$—, or —$CH_2CH_2OCH_2CH_2$—.

Further preferred in the present invention is a process as described above wherein:

$R^1$ and $R^2$ are methyl;

$R^4$ and $R^7$ are benzyl, fluorobenzyl, pyrrolylmethyl, methoxybenzyl, isobutyl, n-octyl, n-hexyl, dimethylaminobenzyl, thienylmethyl, pyridylmethyl, or naphthylmethyl.

The present invention also provides compounds of formula (II):

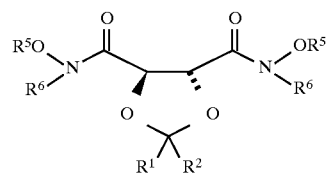

wherein:

$R^5$ and $R^6$ are independently $C_1$–$C_4$ alkyl or benzyl; and $R^1$ and $R^2$ are independently: H, $C_1$–$C_4$ alkyl, $C_1$–$C_4$ alkoxy, $C_6$–$C_{10}$ aryl, $C_7$–$C_{14}$ arylalkyl, $C_1$–$C_4$ haloalkyl, $C_3$–$C_7$ cycloalkyl, or can be taken together to be keto, or, alternatively, $R^1$ and $R^2$ can be taken together with the carbon to which they are attached to form a 3–7 membered saturated carbocyclic ring system.

The processes of the present invention are useful for the preparation of compounds useful as intermediates for the synthesis of cyclic HIV protease inhibitors, including cyclic urea HIV protease inhibitors. Such cyclic HIV protease inhibitors are disclosed in copending commonly assigned U.S. patent application Ser. No. 08/197,630, Lam et al., filed Feb. 16, 1994 and Lam et al., PCT International Publication Number WO 93/07,128, the disclosures of which are incorporated herein by reference. Such cyclic HIV protease inhibitors are useful for the inhibition of HIV and the treatment of HIV infection. Such cyclic HIV protease inhibitors are also useful for the inhibition of HIV in an ex vivo sample containing HIV or expected to be exposed to HIV. Thus, such cyclic HIV protease inhibitors may be used to inhibit HIV present in a body fluid sample (for example, a serum or semen sample) which contains or is suspected to contain or be exposed to HIV. Such cyclic HIV protease inhibitors are also useful as standard or reference compounds for use in tests or assays for determining the ability of an agent to inhibit viral replication and/or HIV protease, for example in a pharmaceutical research program. Thus, such cyclic HIV protease inhibitors may be used as a control or reference compound in such assays and as a quality control standard. Such cyclic HIV protease inhibitors may be provided in a commercial kit or container for use as such standard or reference compound. Since such cyclic HIV protease inhibitors exhibit specificity for HIV protease, they may also be useful as diagnostic reagents in diagnostic assays for the detection of HIV protease. Thus, inhibition of the protease activity in an assay by such a cyclic HIV protease inhibitor would be indicative of the presence of HIV protease and HIV virus.

The compounds of formula (I) to (V) of the present invention contain a cyclic hydroxyl protecting group —OC$(R^1)(R^2)$O—. As used herein, the term "cyclic hydroxyl protecting group" refers to any group known in the art of organic synthesis for the protection of 1,2-diol groups. Such protecting groups include, but are not limited to, those listed in Greene and Wuts, "Protective Groups in Organic Synthesis", John Wiley & Sons, New York (1991), the disclosure of which is hereby incorporated by reference. The 1,2-diol protecting groups can include, but are not limited to cyclic acetals (ketals), cyclic carbonates and cyclic ortho esters. Exemplary are methylene acetal, ethylidene acetal, 2,2,2-trichloroethylidene acetal, acetonide, cycloheptylidene ketal, cyclopentylidene ketal, cyclohexylidene ketal, benzylidene acetal, phenanthrylidene, methoxymethylene acetal, dimethoxy methylene ortho ester, and cyclic carbonates.

The following terms and abbreviations are used herein and are defined as follows. The abbreviation "THF" as used herein means tetrahydrofuran. The abbreviation "DIBAl" means diisobutylaluminum hydride. The abbreviation "RaNi" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "BOC" means t-butyl carbamate. The abbreviation "CBZ" means benzyl carbamate.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. Depending on the particular reaction step, suitable solvents for a particular reaction step may be selected and may include protic or aprotic solvents, including but not limited to polar aprotic organic solvents. Depending on the particular reaction step, suitable solvents for a particular reaction step may be selected and may include, but are not limited to, toluene, pyridine, dimethylsulfoxide (DMSO), N,N-dimethylformamide (DMF), N,N-dimethylacetamide (DMAC), diethyl ether, benzene, tetrahydrofuran, ethanol, water, methylene chloride, ethylacetate, diethyl ether, benzene, or tetrahydrofuran. Suitable solvents may include chlorinated organic solvents which include, but are not limited to, chloroform, methylene chloride, tetrachloroethane, butyl chloride and dichloroethane. Suitable non-chlorinated organic solvents may include, but are not limited to tetrahydrofuran (THF), diethyl ether, or toluene.

Suitable protic solvents may include, by way of example and without limitation, water, methanol, and ethanol.

Suitable aprotic solvents may include, by way of example and without limitation, dimethylformamide (DMF), dimethylacetamide (DMAC), 1,3-dimethyl-3,4,5,6-tetrahydro-2 (1H)-pyrimidinone (DMPU), 1,3-dimethyl-2-imidazolidinone (DMI), N-methylpyrrolidinone (NMP), tetrahydrofuran (THF), methylene chloride, dimethoxyethane, ether, or hexanes.

As used herein, the term "carboxyl activating agent" means any reagent or combination of reagents that will activate a carboxylic acid for formation of an amide bond. Exemplary carboxyl activating agents include, by way of example and without limitation, 1,1'-carbonyldiimidazole, N,N-dicyclohexylcarbodiimide, 1-(3-dimethylaminopropyl)-3-ethylcarbodiiide hydrochloride, thionyl chloride, oxalyl chloride, and isobutylchloroformate. Some of these reagents (such as N,N-dicyclohexylcarbodiimide) can be enhanced by the addition of 1-hydroxybenzotriazole.

Carboxyl activating agents include any agent or combination of agents which will effect the formation of an activated carboxyl group and/or any such agent as commonly used in the art of protein or synthetic organic chemistry to effect the formation of peptide or amide bonds. Such agents include, by way of example and without limitation, those listed in Gross and Meienhofer, "The Peptides: Analysis, Synthesis, Biology, Vol. 1", Academic Press, New York (1979), the disclosure of which is hereby incorporated by reference. Such agents include, but are not limited to, anhydrides, azides, cyanides, carbodiimides, aryl esters, carbonyldiimidazole, phosgene, oxalylchloride, thionylchloride, thionylbromide, and alcohols. In general, suitable carboxyl activating agents include, but are not limited to: N-ethyloxycarbonyl-2-ethyloxy-1,2-dihydroquinoline (EEDQ), N-isobutyloxycarbonyl-2-isobutyloxycarbonyl-1,2-dihydroquinoine (IIDQ), or an alkyl chlorocarbonate, such as isobutyl chlorocarbonate, which yield mixed anhydride activated carboxyl groups; diphenylphosphorazidate which yields azide activated carboxyl groups; and carbonyldiimidazole, ethoxyacetylene, or dicyclohexylcarbodiimide (the latter two preferrably reacted in the presence of 1-hydroxybenzotriazole or N-hydroxysuccinimide) which yield active ester activated carboxyl groups.

As used herein, the term "nucleophilic organometallic reagent" or "organometallic reagent" means any organometallic reagent that can add a $R^4$- or $R^7$-substituent to amides of the structure of compound (II) to yield a compound of formula (III). Such organometallic reagent may be represented by the formula $R^4$-M or $R^7$-M, where M is a suitable metal or metal halide, for example, lithium, magnesium halide, zinc, copper, or other suitable metallic group, as is understood in the art of organic synthesis. Exemplary nucleophilic organometallic reagents include, by way of example and without limitation: benzyllithium, n-butyllithium, sec-butyllithium, tert-butyllithium, methylmagnesium bromide, vinyllithium, allyllithium, ethyllithium, phenylthiomethyllithium, 2-furyllithium, butynyllithium, benzylmagnesium chloride, and phenylmagnesium chloride, and substituted derivatives thereof.

As used herein, the term "reducing agent" means any reagent and/or conditions or combinations of such reagents and/or conditions that may be used to convert an oxime group to an amine. Exemplary oxime reducing agents include, by way of example and without limitation: diisobutylaluminum hydride, lithium aluminum hydride, borane, and Raney nickel and hydrogen.

Such reducing agents include those listed in March, "Advanced Organic Chemistry: Reactions, Mechanisms and Structure" 3rd Edition, John Wiley & Sons, New York (1985), the disclosure of which is hereby incorporated by reference. Reducing agents include, but are not limited to, lithium aluminum hydride (LAH), $AlH_3$, diisobutyl aluminum hydride (DIBAL-H), $NaAlEt_2H_2$, sodium bis(2-methoxyethoxy)aluminum hydride (RED-AL®).

As used herein, the term "amine protecting group" (or "N-protected") refers to any group known in the art of organic synthesis for the protection of amine groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10, 10-tetrahydrothio-xanthyl)]methyl carbamate;

2-trimethylsilylethyl carbamate; 2-phenylethyl carbamate; 1,1-dimethyl-2,2-dibromoethyl carbamate; 1-methyl-1-(4-biphenylyl)ethyl carbamate; benzyl carbamate; p-nitrobenzyl carbamate; 2-(p-toluenesulfonyl)ethyl carbamate; m-chloro-p-acyloxybenzyl carbamate; 5-benzyisoxazolylmethyl carbamate; p-(dihydroxyboryl) benzyl carbamate; m-nitrophenyl carbamate; o-nitrobenzyl carbamate; 3,5-dimethoxybenzyl carbamate; 3,4-dimethoxy-6-nitrobenzyl carbamate; N'-p-toluenesulfonylaminocarbonyl; t-amyl carbamate; p-decyloxybenzyl carbamate; diisopropylmethyl carbamate; 2,2-dimethoxycarbonylvinyl carbamate; di(2-pyridyl)methyl carbamate; 2-furanylmethyl carbamate; phthalimide; dithiasuccinimide; 2,5-dimethylpyrrole; benzyl; 5-dibenzylsuberyl; triphenylmethyl; benzylidene; diphenylmethylene; or methanesulfonamide.

As used herein, the term "hydroxy protecting group" (or "O-protected") refers to any group known in the art of organic synthesis for the protection of hydroxyl groups. Such protecting groups include those listed in Greene and Wuts, "Protective Groups in Organic Synthesis", John Wiley & Sons, New York (1991), the disclosure of which is hereby incorporated by reference. The hydroxy protecting groups are base-stable and can include, but are not limited to acyl types, aromatic carbamate types and alkyl types. Exemplary are methyl, methoxymethyl (MOM), methylthiomethyl, benzyloxymethyl, t-butoxymethyl, 2-methoxyethoxymethyl, 2,2,2-trichloroethoxymethyl, 2-(trimethylsilyl)ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Suitable hydroxy protecting groups may include the following protecting groups as ethers: tetrahydropyranyl, triphenylmethyl, benzyl, tetrahydrofuranyl, allyl, methoxymethyl (MOM), benzyloxymethyl, p-methoxybenzyloxymethyl, 2-trimethylsilylethoxymethyl (SEM), t-butoxymethyl, methylthiomethyl, 2-methoxyethoxymethyl, trichloroethoxymethyl, t-butyl, p-methoxybenzyl, t-butyldimethylsilyl, o-nitrobenzyl, p-methoxyphenyldiphenylmethyl, p-nitrobenzyl, triisopropylsilyl, t-butyldiphenylsilyl.

Conditions to remove tetrahydropyranyl, triphenylmethyl, tetrahydrofuranyl, methoxymethyl, benzyloxymethyl, p-methoxybenzyloxymethyl, 2-trimethylsilylethoxymethyl, t-butoxymethyl, methylthiomethyl, 2-methoxyethoxymethyl, trichloroethoxymethyl, t-butyl, p-methoxyphenyldiphenylmethyl, may include: (a) 1–4M HCl in anhydrous or aqueous methanol, ethanol, isopropanol, tetrahydrofuran, dioxane, or diethyl ether; (b) 1–4M H2SO4 in anhydrous or aqueous methanol, ethanol, isopropanol, tetrahydrofuran, dioxane, or diethyl ether; (c) polystyrene sulfonic acid resin in anhydrous or aqueous methanol, ethanol, isopropanol, tetrahydrofuran, dioxane, or diethyl ether; (d) 10–100% trifluoroacetic acid in dichloromethane; or (e) p-toluenesulfonic acid or camphorsulfonic acid in anhydrous or aqueous methanol, ethanol, isopropanol.

Conditions to remove benzyl, benzyloxymethyl, p-methoxybenzyloxymethyl, p-methoxybenzyl, o-nitrobenzyl, p-nitrobenzyl are: hydrogenolysis in the presence of 1–17% palladium on carbon, or palladium black. Conditions to remove o-nitrobenzyl group include irradiation of the compound at 320 nm wavelength for 5–60 minutes.

Conditions to remove 2-trimethylsilylethoxymethyl, t-butyldimethylsilyl, triisopropylsilyl, t-butyldiphenylsilyl may include: treatment of the compound with tetrabutylammonium fluoride; or hydrogen flouride pyridine complex in THF, DMF or dimethylpropyleneurea.

Conditions to remove allyl may include: isomerization of the allyl ether with $[Ir(COD)(Ph_2MeP)_2]PF_6$ or $(Ph_3P)_3RhCl$ in tetrahydrofuran, diethyl ether or dioxane followed by hydrolysis with aqueous $HgCl_2$.

All of the above mentioned deprotection reactions may be carried out at temperetaures ranging from 0 degree C. to a solvent reflux.

The compounds herein described may have asymmetric centers. Unless otherwise indicated, all chiral, diastereomeric and racemic forms are included in the present invention. Geometric isomers of C=N double bonds, and the like can also be present in the compounds described herein, and all such stable isomers are contemplated in the present invention. It will be appreciated that compounds of the present invention contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific sterochemistry or isomer form is specifically indicated.

When any variable (for example, but not limited to, $R^{11}$ and $R^{12}$) occurs more than one time in any constituent or in any formula, its definition on each occurrence is independent of its definition at every other occurrence. Thus, for example, if a group is shown to be substituted with 0–2 $R^{11}$, then said group may optionally be substituted with up to two $R^{11}$ and $R^{11}$ at each occurrence is selected independently from the defined list of possible $R^{11}$.

Combinations of substituents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example $-C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon—carbon bonds which may occur in any stable point along the chain, such as ethenyl, propenyl, and the like; and "alkynyl" is intended to include hydrocarbon chains of either a straight or branched configuration and one or more triple carbon—carbon bonds which may occur in any stable point along the chain, such as ethynyl, propynyl and the like. "Alkylcarbonyl" is intended to include an alkyl group of an indicated number of carbon atoms attached through a carbonyl group to the residue of the compound at the designated location. "Alkylcarbonylamino" is intended to include an alkyl group of an indicated number of carbon atoms attached through a carbonyl group to an amino bridge, where the bridge is attached to the residue of the compound at the designated location. "Alkylcarbonyloxy" is intended to include an alkyl group of an indicated number of carbon atoms attached to a carbonyl group, where the carbonyl group is attached through an oxygen atom to the residue of the compound at the designated location.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl) aryl" is intended to refer to a $C_1$–$C_3$ alkyl group which is attached through an aryl ring to the residue of the indicated compound; the term "aryl($C_1$–$C_3$ alkyl)" is intended to refer to an aryl group attached through a $C_1$–$C_3$ alkyl group to the residue of the indicated compound.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridinyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, or isatinoyl. Also included are fused ring and spiro compounds containing, for example, the above heterocycles. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of a given formula via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "amino acid" as used herein means an organic compound containing both a basic amino group and an acidic carboxyl group. Included within this term are natural amino acids, modified and unusual amino acids, as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The methods of the present invention may be further understood by reference to Scheme 1.

Scheme 1

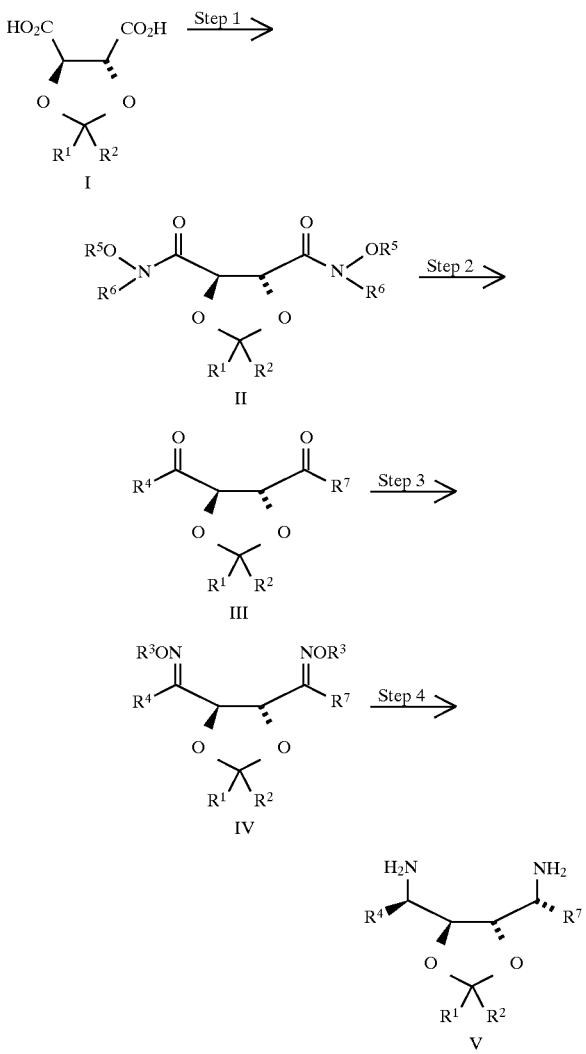

It is the object of the present invention to provide an improved process for the preparation of diamine intermediates for the synthesis of HIV protease inhibitors including cyclic carbonyls.

Step 1: Diamide Formation: Preparation of Compound of Formula (II)

This step comprises: (a) the conversion of a compound of formula (I) to a bisamide using an carboxyl activating agent by reacting a compound of formula (I) in a suitable solvent, preferably an aprotic solvent, at a suitable temperature with preferably at least about two molar equivalents (more preferably 2–100 or 2–20 equivalents) of a suitable carboxyl activating agent for a suitable length of time, followed by; (b) treatment of the activated acyl intermediate with at least about two molar equivalents (more preferably 2–100 or 2–20 equivalents) of a N,O-dialkylhydroxylamine of formula $R^6NHOR^5$ to form a compound of formula (II). By way of general guidance, in step (Ia), compound (I) in an aprotic solvent may be contacted, with agitation at 0° to 100° C. for 1–24 hr under an inert atmosphere, with 2–3 molar equivalents of a carboxylic acid activating agent, followed by step (1b), treatment in situ of the resulting intermediate with a N,O-dialkylhydroxylamine at 0°–50° C. for 1–24 hr to form compound (II). Compound (II) may be separated from the reaction mixture, for example, by washing with dilute acid and water and concentrating the organic layer. Compound (II) optionally may be recrystallized from a suitable solvent mixture, such as ethyl acetate/hexane, prior to use in step (2).

A preferred reaction temperature for step (1) is 250° C.

A preferred reaction time for step (1a) is about 5–7 hr and for step (1b) is about 12–18 hr.

Preferred solvents for step (1) include methylene chloride, tetrahydrofuran, N,N-dimethylformamide, and dimethoxyethane. A more preferred solvent is methylene chloride.

Preferred carboxyl activating agents for step (1) include 1,1'-carbonyldiimidazole, thionyl chloride, oxalyl chloride, isobutylchloroformate and 1-(3-dimethylaminopropyl)-3-ethylcarbodiimide hydrochloride. A more preferred carboxyl activating agent is 1,1'-carbonyldiimidazole.

A preferred N,O-dialkylhydroxylamine is N,O-dimethylhydroxylamine hydrochloride.

Step (2): Ketone Formation: Preparation of Compound of Formula (III)

This step comprises alkylation of the amide carbonyl of a compound of formula (II) by contacting a compound of formula (II) in a suitable solvent, preferably an aprotic solvent, with preferably at least about two equivalents (more preferably 2–100 or 2–20 equivalents) of a nucleophilic organometallic reagent, said nucleophilic organometallic reagent being suitable for the addition of a $R^4$- or $R^7$-substituent to amides of the structure of compound (II), at a suitable temperature, to form a compound of formula (III). Alkylation of the amide carbonyl may be carried out using an organometallic reagent of the formula $R^4$-M and/or $R^7$-M, where M is a suitable metal halide, such as lithium or magnesium halide. By way of general guidance, compound (II) in a suitable aprotic solvent at −78°–100° C. may be contacted with 2–10 molar equivalents of a nucleophile, $R^4$-M and/or $R^7$-M, for 0.1–24 hr to form compound (III). Compound (III) may be isolated by washing this reaction mixture with dilute acid and concentrating the organic layer. Compound (III) may optionally be purified by chromatography on silica gel prior to use in step (3).

A preferred reaction temperature is 0° C.

Preferred reaction solvents include tetrahydrofuran, ether, or hexanes. A more preferred solvent is tetrahydrofuran.

It is preferred that 3–6 molar equivalents of nucleophilic organometallic reagent $R^4$-M or $R^7$-M is used. The preferred nucleophilic organometallic reagent is an organolithium or organomagnesium halide (i.e., M is lithium or magnesium halide. Preferred nucleophilic organometallic reagents include benzyllithium, n-butyllithium, sec-butyllithium, tert-butyllithium, methylmagnesium bromide, octylmagnesium bromide, hexylmagnesium bromide, vinyllithium, allyllithium, ethyllithium, phenylthiomethyllithium, 2-furyllithium, butynyllithium, benzylmagnesium chloride, and phenylmagnesium chloride, and subsituted derivatives thereof. It is preferred that 4–7 molar equivalents of $R^4$ and/or $R^7$ be used.

Step (3): Oxime Formation: Preparation of Compound of Formula (IV)

This step comprises reacting a ketone compound of formula (III) in a suitable solvent, preferably a protic solvent, for a sufficient period of time at a suitable temperature, with preferably at least about two equivalents (more preferably 2–100 or 2–20 equivalents) of an hydroxylamine of formula $NH_2OR^3$, to form an oxime compound of formula (IV). Said hydroxylamine is preferably an acid salt, and more preferably is a hydroxlamine hydrochloride. By way of general guidance, compound (III) in a polar protic solvent may be contacted with agitation at 0° to 100° C. with an hydroxylamine for 1–48 hr to form compound (IV). Compound (IV) may be isolated by extracting the reaction mixture with an organic solvent, such as ethyl acetate, and concentrating the organic layer. The residue may optionally be purified by chromatography on silica gel to give predominantly the anti:anti oxime isomer for use in step (4).

A preferred reaction temperature is about 25° C.

A preferred reaction time is 24 hr.

Preferred solvents include water, methanol and ethanol. A more preferred solvent is aqueous ethanol.

A preferred hydroxylamine is hydroxylamine hydrochloride.

The reaction in step (3) is optionally, but preferably carried out in the absence of a base. For example, when sodium acetate was added to neutralize the acid evolved, significantly greater amounts of the undesired oxime isomers resulted.

Step (4): Amine Formation: Preparation of Compound of Formula (V)

This step comprises contacting an oxime compound of formula (IV) in a suitable solvent for a sufficient period of time at a suitable temperature with a suitable reducing agent to effect the conversion of the oxime groups in the compound of formula (IV) to amine groups, to obtain a compound of formula (V). By way of general guidance, compound (IV) in a suitable solvent may be contacted with agitation at about −10° to 100° C. for about 0.1–72 hr with a reducing agent to form compound (V) which can be optionally isolated in the free base or salt form.

Preferred reducing agents include lithium aluminum hydride, borane, diisobutoxyaluminum hydride, or catalytic hydrogenation in the presence of a Raney nickel catalyst. A more preferred reducing agent is diisobutoxyaluminum hydride.

The suitable solvent will depend on the choice of reducing agent. Preferred solvents for diisobutyoxyaluminum hydride reduction include tetrahydrofuran, ether, or toluene. A more preferred solvent for this reagent is toluene. If catalytic hydrogenation over Raney nickel is chosen, then the preferred solvent includes ethanol.

A preferred reaction temperature is 25°–35° C.

A preferred reaction time is about 18 hr.

A preferred isolation method when the reducing agent is diisobutoxyaluminum hydride and the reaction solvent is toluene is stirring the reaction mixture with saturated sodium potassium tartrate and extraction with an organic solvent, for example ethyl acetate, and concentrating the organic layer. The residue can be optionally purified by chromatography on silica gel to give the diamine (V) with the desired (R,S,S,R) stereochemistry.

The synthetic processes of the present invention can be employed for the synthesis of HIV protease inhibitors such as those disclosed in Jadhav et al., WO 93/07,128 and European Patent Application 402,646 A1. The disclosure of each of the references cited herein is hereby incorporated herein by reference.

The present invention may be further exemplified by reference to Scheme 2.

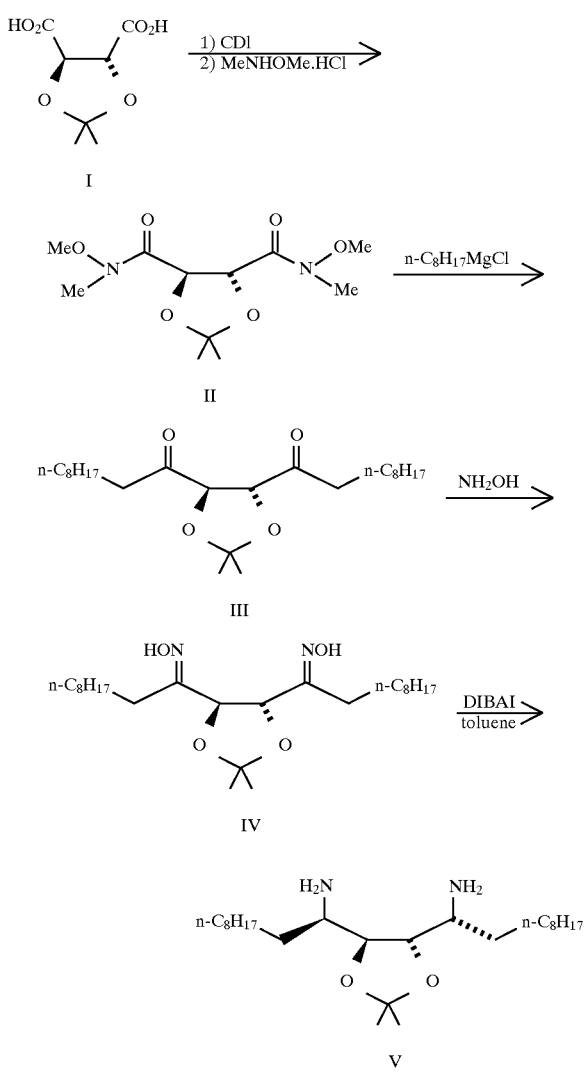

With a judicious selection of reagents, as is well appreciated to one skilled in the art of organic synthesis, the claimed process can be performed in a straightforward manner to yield the compounds of formulas (II), (III), (IV) and (V).

Each of the references cited herein are hereby incorporated herein by reference.

The following examples are meant to be illustrative of the present invention. These examples are presented to exemplify the invention and are not to be construed as limiting the invention's scope.

EXAMPLE 1

(formula (II) wherein $R^1$, $R^2$, $R^5$, and $R^6$=methyl)

Step 1

To a solution of L-2,3-isopropylidene tartaric acid (30 g, 157.8 mmol) in methylene chloride (1 L) was added 1,1'-carbonyldiimidazole (60 g, 370.0 mmol). After stirring for 6 hr, of N,O-dimethylhydroxylamine hydrochloride (34.0 g, 350 mmol) was added and the resulting solution was stirred overnight. The solvent was partially removed under reduced pressure and the residue was diluted with ethyl acetate, The solution was then acidified with 4N HCl, saturated with NaCl, and extracted with EtOAc. The combined organic layers were washed with brine and dried over MgSO4. The solvent was removed under reduced pressure and the residue was triturated with ethyl acetate and hexanes to give the bis-Weinreb amide (II) (35.6 g, 82%) as a white solid. mp. 78°–80° C. $^1$H NMR (300 MHz, CDCl$_3$) δ 5.16 (s, 2H, CH), 3.70 (s, 6H, OCH$_3$), 3.22 (s, 6H, CH$_3$), 1.52 (s, 6H, CH$_3$); MS (CI,NH$_3$) m/e 277 (M+1);

EXAMPLE 2

(formula (III) wherin $R^1$ and $R^2$=methyl, $R^5$, and $R^6$=octyl)

Step 2

To a solution of the product of Example 1 (4.0 g, 14.5 mmol) in THF (100 mL) was added a solution of 2M octylmagnesium bromide in THF (20 mL, 40 mmol) dropwise. After stirring for 3.5 hr, the solution was quenched with saturated NH$_4$Cl, acidified with 1N HCl, and was extracted with EtOAc. The combined organic layers were washed with brine and dried over MgSO4. The solvent was removed under reduced pressure and the residue was chromatographed on silica gel. Elution with 7.5% ethyl acetate in hexanes gave the bis-octyl ketone (III) (4.86 g, 88%) as an oil. $^1$H NMR (300 MHz, CDCl$_3$) δ 4.55 (s, 2H, CH), 2.64 (dt, 4H, CH$_2$), 1.62 (m, 4H, CH$_2$), 1.42 (s, 6H, CH$_3$), 1.27 (broad s, 20H, CH$_2$), 0.88 (t, 6H, CH$_3$); MS (CI,NH$_3$) m/e 383 (M+1)

EXAMPLE 3

(formula (IV) wherein $R^1$ and $R^2$=methyl, $R^5$, and $R^6$=octyl, $R^3$=H)

Step 3

To a solution of the product of Example 2 (4.65 g, 12.2 mmol) in ethanol (140 mL) and water (35 ml) was added hydroxylamine hydrochloride (2.22 g, 32.2 mmol). After stirring overnight, the solvent was partially removed under reduced pressure, and the residue was diluted with water and extracted with EtOAc. The combined organic layers were washed with brine and dried over MgSO$_4$. The solvent was removed under reduced pressure and the residue was chromatographed on silica gel. Elution with 15% ethyl acetate in hexanes gave the bis-octyl oxime (IV) as a 4.5/1 mixture of the anti:anti/anti:syn oxime isomers (3.76 g, 75%). anti:anti oxime; $^1$H NMR (300 MHz, CDCl$_3$) δ 4.55 (s, 2H, CH), 2.47 (m, 2H, CH$_2$), 2.23 (m, 2H, CH$_2$), 1.59 (br s, 4H, CH$_2$), 1.43 (s, 6H, CH$_3$), 1.26 (broad s, 20H, CH$_2$), 0.88 (t, 6H, CH$_3$); MS (CI,NH$_3$) m/e 413 (M+1).

EXAMPLE 4

(formula (V) wherein $R^1$ and $R^2$=methyl, $R^5$ and $R^6$=octyl)

Step 4

To a solution of the the product of Example 3 (3.68 g, 8.9 mmol) in toluene (70 mL) at 0° C. was added a solution of 1.5M diisobutylaluminum hydride in toluene (53 mL, 80 mmol) over 15 min. The resulting solution was allowed to warm to room temperature. After stirring overnight, the solution was quenched with saturated Rochelle's salt and gently stirred at room temperature. After stirring overnight, the solution was extracted with EtOAc and dried over MgSO$_4$. The solvent was removed under reduced pressure and the residue was chromatographed on silica gel. Elution with 10% methanol in methylene chloride gave the (R,S,S, R) diamine V (2.33 g, 68%) as an oil. $^1$H NMR (300 MHz, CDCl$_3$) δ 3.80 (s, 2H, CH), 2.68 (m, 2H, CH), 1.43 (m, 4H, CH$_2$), 1.41 (s, 6H, CH$_3$), 1.27 (broad s, 24H, CH$_2$), 0.88 (t, 6H, CH$_3$); MS (CI,NH$_3$) m/e 385 (M+1).

The present invention may be embodied in other specific forms without departing from the spirit or essential attributes thereof and, accordingly, reference should be made to the appended claims as further indicating the scope of the invention.

What is claimed is:

1. A process for the preparation of a compound of formula (II):

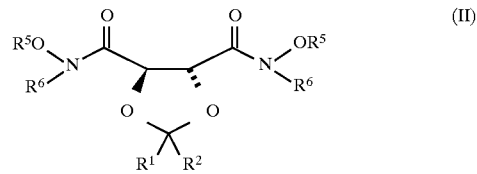

wherein:
$R^5$ and $R^6$ are independently C$_1$–C$_4$ alkyl or benzyl; and
$R^1$ and $R^2$ are independently: H, C$_1$–C$_4$ alkyl, C$_1$–C$_4$ alkoxy, C$_6$–C$_{10}$ aryl, C$_7$–C$_{14}$ arylalkyl, C$_1$–C$_4$ haloalkyl, C$_3$–C$_7$ cycloalkyl, or taken together to form keto, or, alternatively, $R^1$ and $R^2$ are taken together with the carbon to which they are attached to form a 3–7 membered saturated carbocyclic ring system;

said process comprising the step of:
(1) (a) contacting a compound of formula (I):

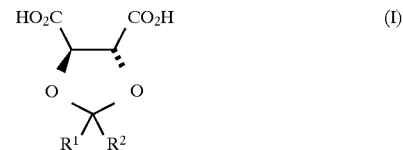

wherein $R^1$ and $R^2$ are defined as above,
in an aprotic solvent with a carboxyl activating agent, followed by; (b) addition of a N,O-dialkylhydroxylamine of formula $R^6$NHOR$^5$, wherein $R^5$ and $R^6$ are defined as above, to form a compound of formula (II).

2. A process of claim 1 wherein:
$R^5$ and $R^6$ are independently C$_1$–C$_4$ alkyl or benzyl; and
$R^1$ and $R^2$ are independently methyl, or ethyl, or, alternatively, $R^1$ and $R^2$ are taken together with the carbon to which they are attached to form cyclopentyl.

3. A process for the preparation of a compound of formula (III):

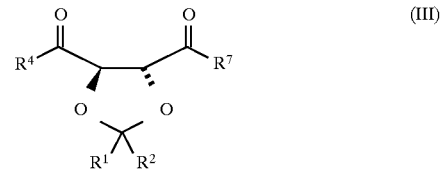

wherein:
$R^1$ and $R^2$ are independently: H, C$_1$–C$_4$ alkyl, C$_1$–C$_4$ alkoxy, C$_6$–C$_{10}$ aryl, C$_7$–C$_{14}$ arylalkyl, C$_1$–C$_4$ haloalkyl, C$_3$–C$_7$ cycloalkyl, or taken together to form keto;
alternatively, $R^1$ and $R^2$ are taken together with the carbon to which they are attached to form a 3–7 membered saturated carbocyclic ring system;
$R^4$ and $R^7$ are independently:

$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ is selected from one or more of the following:
H, keto, halogen, cyano, —$CH_2NR^{13}R^{14}$, —$NR^{13}R^{14}$, —$OR^{13}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, azido;
$C_3$–$C_{10}$ cycloalkyl substituted with 0–2 $R^{12}$;
$C_1$–$C_4$ alkyl substituted with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$;
a $C_5$–$C_{14}$ carbocyclic residue substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is:
H, halogen, cyano, —$CH_2N(R^{13A})R(^{14A})$, —$N(R^{13A})R(^{14A})$, —OH, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, azido, aryl($C_1$–$C_3$ alkyl), a $C_5$–$C_{14}$ carbocyclic residue; or a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or
a 5- or 6-membered heterocyclic ring containing from 1 to 4 heteroatoms independently selected from oxygen, nitrogen or sulfur; or $R^{12}$, when $R^{11}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12}$, when a substituent on nitrogen, is:
phenyl, benzyl, phenethyl, hydroxy, $C_1$–$C_4$ hydroxyalkyl, $C_1$–$C_4$ alkoxy, $C_{1-C4}$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, or $C_1$–$C_4$ haloalkyl;

$R^{12A}$, when a substituent on carbon, is:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13a}$, $C_1$–$C_4$ alkyl substituted with —$NH_2$, —$NH_2$, —NHMe, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, 2-(4-morpholino) ethoxy, or
a 5- or 6-membered heterocyclic ring containing from 1 to 4 heteroatoms independently selected from oxygen, nitrogen or sulfur; or $R^{12A}$, when $R^{11A}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12A}$, when a substituent on nitrogen, is:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, or $C_1$–$C_4$ haloalkyl;

$R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_3$–$C_6$ alkoxyalkyl substituted with 0–3 $R^{11A}$;
an amine protecting group when $R^{13}$ is bonded to N; or
a hydroxy protecting group when $R^{13}$ is bonded to O;

$R^{14}$ is selected from: hydrogen; hydroxy; $C_1$–$C_6$ alkoxy; $C_2$–$C_6$ alkenyl; phenyl; benzyl; an amine protecting group when $R^{14}$ is bonded to N; a hydroxy protecting group when $R^{14}$ is bonded to O; or $C_1$–$C_6$ alkyl substituted with 0–3 groups selected from OH, $C_1$–$C_4$ alkoxy, halogen, $NH_2$, or —NH($C_1$–$C_4$ alkyl);

$R^{13}$ and $R^{14}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{13A}$ and $R^{14A}$ are independently selected from: H or $C_1$–$C_6$ alkyl;

$R^{13A}$ and $R^{14A}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{15}$ is H or $CH_3$;

m is 0, 1 or 2;

said process comprising contacting a compound of formula (II):

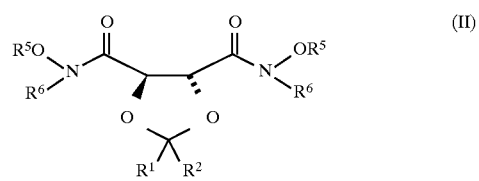

wherein $R^1$ and $R^2$ are defined as above and $R^5$ and $R^6$ are independently $C_1$–$C_4$ alkyl or benzyl, in an aprotic solvent with a nucleophilic organometallic reagent, said nucleophilic organometallic reagent being suitable for the addition of a $R^4$- or $R^7$-substituent to amides of the structure of compound (II), to form a compound of formula (III).

4. A process of claim 3 wherein:

$R^1$ and $R^2$ are methyl, ethyl, or taken together with the carbon to which they are attached to form cyclopentyl;

$R^4$ and $R^7$ are $C_1$–$C_8$ alkyl substituted with 0–1 $R^{11}$;

$R^{11}$ is

H; halogen; —$OR^{13}$;

$C_3$–$C_{10}$ cycloalkyl substituted with 0–2 $R^{12}$;

aryl substituted with 0–2 $R^{12}$; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, or oxazolidinyl, said heterocyclic ring system being substituted with 0–2 $R^{12}$;

$R^{12}$, when a substituent on carbon, is selected from one or more of the following:

benzyloxy, halogen, methyl, $C_1$–$C_4$ alkoxy, $CF_3$, 2-(4-morpholino)ethoxy, cyano, $C_3$–$C_6$ cycloalkoxy, $C_1$–$C_4$ alkyl substituted with —$NR^{13}R^{14}$, or —$NR^{13}R^{14}$;

$R^{12}$, when a substituent on nitrogen, is methyl;

$R^{13}$ is H, $C_1$–$C_4$ alkyl, $C_2$–$C_4$ alkenyl, or benzyl;

$R^{14}$ is H, $CF_3$, $C_1$–$C_4$ alkyl, $C_1$–$C_4$ alkoxy, $C_2$–$C_4$ alkenyl, or benzyl;

$R^{13}$ and $R^{14}$ alternatively join to form —$(CH_2)_4$-, —$(CH_2)_5$-, —$CH_2CH_2N(R^{15})CH_2CH_2$—, or —$CH_2CH_2OCH_2CH_2$—.

5. A process of claim 3 wherein:

$R^1$ and $R^2$ are methyl;

$R^4$ and $R^7$ are benzyl, fluorobenzyl, pyrrolylmethyl, methoxybenzyl, isobutyl, n-octyl, n-hexyl, dimethylaminobenzyl, thienylmethyl, pyridylmethyl, or naphthylmethyl.

6. A process for the preparation of a compound of formula (V):

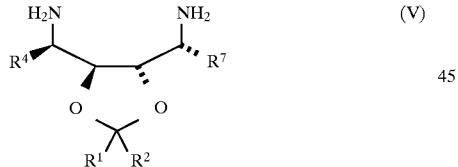

wherein:

$R^1$ and $R^2$ are independently: H, $C_1$–$C_4$ alkyl, $C_1$–$C_4$ alkoxy, $C_6$–$C_{10}$ aryl, $C_7$–$C_{14}$ arylalkyl, $C_1$–$C_4$ haloalkyl, $C_3$–$C_7$ cycloalkyl, or taken together to form keto;

alternatively, $R^1$ and $R^2$ are taken together with the carbon to which they are attached to form a 3–7 membered saturated carbocyclic ring system;

$R^4$ and $R^7$ are independently:

$C_1$–$C_8$ alkyl substituted with 0–3 $R^{11}$;

$C_2$–$C_8$ alkenyl substituted with 0–3 $R^{11}$;

$C_2$–$C_8$ alkynyl substituted with 0–3 $R^{11}$;

a $C_3$–$C_{14}$ carbocyclic ring system substituted with 0–3 $R^{11}$ or 0–3 $R^{12}$; or a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ is selected from one or more of the following:

H, keto, halogen, cyano, —$CH_2NR^{13}R^{14}$, —$NR^{13}R^{14}$, —$OR^{13}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, 2-(4-morpoholino) ethoxy, azido;

$C_3$–$C_{10}$ cycloalkyl substituted with 0–2 $R^{12}$;

$C_1$–$C_4$ alkyl substituted with 0–2 $R^{12}$;

aryl($C_1$–$C_3$ alkyl)-, substituted with 0–2 $R^{12}$;

$C_2$–$C_6$ alkoxyalkyl-, substituted with 0–2 $R^{12}$;

a $C_5$–$C_{14}$ carbocyclic residue substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is:

H, halogen, cyano, —$CH_2N(R^{13A})R(^{14A})$, —$N(R^{13A})R(^{14A})$, —OH, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, azido, aryl($C_1$–$C_3$ alkyl), a $C_5$–$C_{14}$ carbocyclic residue; or a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or a 5- or 6-membered heterocyclic ring containing from 1 to 4 heteroatoms independently selected from oxygen, nitrogen or sulfur; or $R^{12}$, when $R^{11}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12}$, when a substituent on nitrogen, is:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, or $C_1$–$C_4$ haloalkyl;

$R^{12A}$, when a substituent on carbon, is:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13a}$, $C_1$–$C_4$ alkyl substituted with —$NH_2$, —$NH_2$, —NHMe, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or
a 5- or 6-membered heterocyclic ring containing from 1 to 4 heteroatoms independently selected from oxygen, nitrogen or sulfur;

$R^{12A}$, when $R^{11A}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12A}$, when a substituent on nitrogen, is:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, or $C_1$–$C_4$ haloalkyl;

$R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_3$–$C_6$ alkoxyalkyl substituted with 0–3 $R^{11A}$;
an amine protecting group when $R^{13}$ is bonded to N; or
a hydroxy protecting group when $R^{13}$ is bonded to O;

$R^{14}$ is selected from: hydrogen; hydroxy; $C_1$–$C_6$ alkoxy; $C_2$–$C_6$ alkenyl; phenyl; benzyl; an amine protecting group when $R^{14}$ is bonded to N; a hydroxy protecting group when $R^{14}$ is bonded to O; or $C_1$–$C_6$ alkyl substituted with 0–3 groups selected from OH, $C_1$–$C_4$ alkoxy, halogen, $NH_2$, or —$NH(C_1$–$C_4$ alkyl);

$R^{13}$ and $R^{14}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{13A}$ and $R^{14A}$ are independently selected from: H or $C_1$–$C_6$ alkyl;

$R^{13A}$ and $R^{14A}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{15}$ is H or $CH_3$;
m is 0, 1 or 2;
said process comprising contacting a compound of formula (IV):

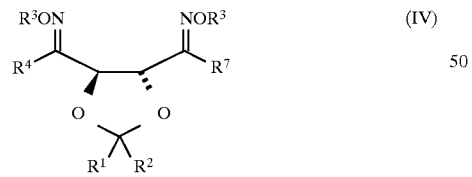

wherein $R^1$, $R^2$, $R^4$ and $R^7$ are defined as above and $R^3$ is hydrogen, $C_1$–$C_6$ alkyl, benzyl, arylcarbonyl or ($C_1$–$C_6$ alkyl)carbonyl;
in a suitable solvent with a reducing agent to effect the conversion of the oxime groups in the compound of formula (IV) to amine groups, to obtain a compound of formula (V).

7. A process of claim 6 wherein:
$R^1$ and $R^2$ are methyl, ethyl, or taken together with the carbon to which they are attached to form cyclopentyl;
$R^4$ and $R^7$ are $C_1$–$C_8$ alkyl substituted with 0–1 $R^{11}$;
$R^{11}$ is H; halogen; —$OR^{13}$;
$C_3$–$C_{10}$ cycloalkyl substituted with 0–2 $R^{12}$;
aryl substituted with 0–2 $R^{12}$; or
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, or oxazolidinyl, said heterocyclic ring system being substituted with 0–2 $R^{12}$;

$R^{12}$, when a substituent on carbon, is selected from one or more of the following:
benzyloxy, halogen, methyl, $C_1$–$C_4$ alkoxy, $CF_3$, 2-(4-morpholino)ethoxy, cyano, $C_3$–$C_6$ cycloalkoxy, $C_1$–$C_4$ alkyl substituted with —$NR^{13}R^{14}$, or —$NR^{13}R^{14}$;

$R^{12}$, when a substituent on nitrogen, is methyl;
$R^{13}$ is H, $C_1$–$C_4$ alkyl, $C_2$–$C_4$ alkenyl, or benzyl;
$R^{14}$ is H, $CF_3$, $C_1$–$C_4$ alkyl, $C_1$–$C_4$ alkoxy, $C_2$–$C_4$ alkenyl, or benzyl;
$R^{13}$ and $R^{14}$ alternatively join to form —$(CH_2)_4$-, —$(CH_2)_5$-, —$CH_2CH_2N(R^{15})CH_2CH_2$—, or —$CH_2CH_2OCH_2CH_2$—.

8. A process of claim 6 wherein:
$R^1$ and $R^2$ are methyl;
$R^4$ and $R^7$ are benzyl, fluorobenzyl, pyrrolylmethyl, methoxybenzyl, isobutyl, n-octyl, n-hexyl, dimethylaminobenzyl, thienylmethyl, pyridylmethyl, or naphthylmethyl.

9. A process for preparation of compounds of formula (V):

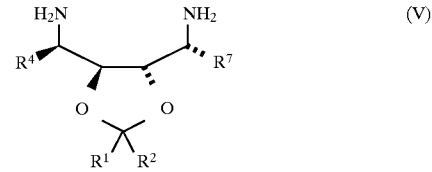

wherein:
$R^1$ and $R^2$ are independently: H, $C_1$–$C_4$ alkyl, $C_1$–$C_4$ alkoxy, $C_6$–$C_{10}$ aryl, $C_7$–$C_{14}$ arylalkyl, $C_1$–$C_4$ haloalkyl, $C_3$–$C_7$ cycloalkyl, or taken together to form keto;
alternatively, $R^1$ and $R^2$ are taken together with the carbon to which they are attached to form a 3–7 membered saturated carbocyclic ring system;
$R^4$ and $R^7$ are independently:
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ is selected from one or more of the following:
H, keto, halogen, cyano, —$CH_2NR^{13}R^{14}$, —$NR^{13}R^{14}$, —$OR^{13}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, azido;
$C_3$–$C_{10}$ cycloalkyl substituted with 0–2 $R^{12}$;

$C_1$–$C_4$ alkyl substituted with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$;
a $C_5$–$C_{14}$ carbocyclic residue substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is:
H, halogen, cyano, —$CH_2N(R^{13A})R(^{14A})$, —$N(R^{13A})R(^{14A})$, —OH, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, azido, aryl($C_1$–$C_3$ alkyl), a $C_5$–$C_{14}$ carbocyclic residue; or a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or
a 5- or 6-membered heterocyclic ring containing from 1 to 4 heteroatoms independently selected from oxygen, nitrogen or sulfur; or $R^{12}$, when $R^{11}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12}$, when a substituent on nitrogen, is:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, or $C_1$–$C_4$ haloalkyl;

$R^{12A}$, when a substituent on carbon, is:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13a}$, $C_1$–$C_4$ alkyl substituted with —$NH_2$, —$NH_2$, —NHMe, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or
a 5- or 6-membered heterocyclic ring containing from 1 to 4 heteroatoms independently selected from oxygen, nitrogen or sulfur; or $R^{12A}$, when $R^{11A}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12A}$, when a substituent on nitrogen, is:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, or $C_1$–$C_4$ haloalkyl;

$R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_3$–$C_6$ alkoxyalkyl substituted with 0–3 $R^{11A}$;
an amine protecting group when $R^{13}$ is bonded to N; or
a hydroxy protecting group when $R^{13}$ is bonded to O;

$R^{14}$ is selected from: hydrogen; hydroxy; $C_1$–$C_6$ alkoxy; $C_2$–$C_6$ alkenyl; phenyl; benzyl; an amine protecting group when $R^{14}$ is bonded to N; a hydroxy protecting group when $R^{14}$ is bonded to O; or $C_1$–$C_6$ alkyl substituted with 0–3 groups selected from OH, $C_1$–$C_4$ alkoxy, halogen, $NH_2$, or —$NH(C_1$–$C_4$ alkyl);

$R^{13}$ and $R^{14}$ alternatively join to form —$(CH_2)_4$-, —$(CH_2)_5$-, —$CH_2CH_2N(R^{15})CH_2CH_2$—, or —$CH_2CH_2OCH_2CH_2$—; $R^{13A}$ and $R^{14A}$ are independently selected from: H or $C_1$–$C_6$ alkyl;

$R^{13A}$ and $R^{14A}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{15}$ is H or $CH_3$;

m is 0, 1 or 2;

said process comprising the following steps:
(1) (a) contacting a compound of formula (I):

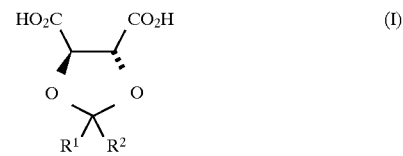

in an aprotic solvent with a carboxyl activating agent, followed by; (b) addition of of a N,O-dialkylhydroxylamine of formula $R^6NHOR^5$, to form a compound of formula (II):

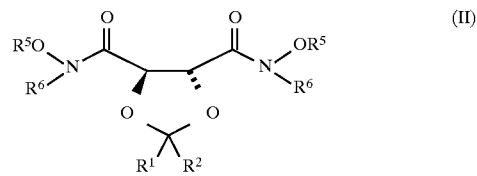

wherein $R^1$ and $R^2$ are defined as above and $R^5$ and $R^6$ are independently $C_1$–$C_4$ alkyl or benzyl;

(2) contacting a compound of formula (II) in an aprotic solvent with a nucleophilic organometallic reagent, said nucleophilic organometallic reagent being suitable for the addition of a $R^4$- or $R^7$-substituent to amides of the structure of compound (II), to form a compound of formula (III):

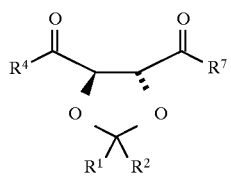

(III)

wherein $R^1$, $R^2$, $R^4$ and $R^7$ are defined as above;

(3) reacting a compound of formula (III) in a protic solvent with a hydroxylamine of formula $NH_2OR^3$, to form a compound of formula (IV):

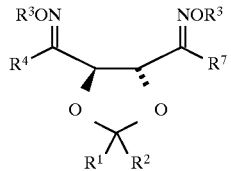

(IV)

wherein $R^1$, $R^2$, $R^4$ and $R^7$ are defined as above and $R^3$ is hydrogen, $C_1$–$C_6$ alkyl, benzyl, arylcarbonyl or ($C_1$–$C_6$ alkyl)carbonyl;

(4) contacting a compound of formula (IV) in a suitable solvent with a reducing agent to effect the conversion of the oxime groups in the compound of formula (IV) to amine groups, to obtain a compound of formula (V).

10. A process for the preparation of compounds of formula (IV):

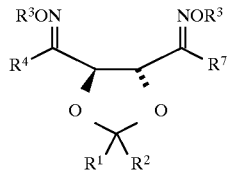

(IV)

wherein:

$R^1$ and $R^2$ are independently: H, $C_1$–$C_4$ alkyl, $C_1$–$C_4$ alkoxy, $C_6$–$C_{10}$ aryl, $C_7$–$C_{14}$ arylalkyl, $C_1$–$C_4$ haloalkyl, $C_3$–$C_7$ cycloalkyl, or taken together to form keto;

alternatively, $R^1$ and $R^2$ are taken together with the carbon to which they are attached to form a 3–7 membered saturated carbocyclic ring system;

$R^3$ is hydrogen, $C_1$–$C_6$ alkyl, benzyl, arylcarbonyl or ($C_1$–$C_6$ alkyl)carbonyl;

$R^4$ and $R^7$ are independently:
  $C_1$–$C_8$ alkyl substituted with 0–3 $R^{11}$;
  $C_2$–$C_8$ alkenyl substituted with 0–3 $R^{11}$;
  $C_2$–$C_8$ alkynyl substituted with 0–3 $R^{11}$;
  a $C_3$–$C_{14}$ carbocyclic ring system substituted with 0–3 $R^{11}$ or 0–3 $R^{12}$; or
  a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ is selected from one or more of the following:
  H, keto, halogen, cyano, —$CH_2NR^{13}R^{14}$, —$NR^{13}R^{14}$, —$OR^{13}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, azido;

$C_3$–$C_{10}$ cycloalkyl substituted with 0–2 $R^{12}$;
$C_1$–$C_4$ alkyl substituted with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$;
a $C_5$–$C_{14}$ carbocyclic residue substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is:
  H, halogen, cyano, —$CH_2N(R^{13A})R^{(14A)}$, —$N(R^{13A})R^{(14A)}$, —OH, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, azido, aryl($C_1$–$C_3$ alkyl), a $C_5$–$C_{14}$ carbocyclic residue; or a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or
  a 5- or 6-membered heterocyclic ring containing from 1 to 4 heteroatoms independently selected from oxygen, nitrogen or sulfur; or $R^{12}$, when $R^{11}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12}$, when a substituent on nitrogen, is:
  phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, or $C_1$–$C_4$ haloalkyl;

$R^{12A}$, when a substituent on carbon, is:
  phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13a}$, $C_1$–$C_4$ alkyl substituted with —$NH_2$, —$NH_2$, —NHMe, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or
  a 5- or 6-membered heterocyclic ring containing from 1 to 4 heteroatoms independently selected from oxygen, nitrogen or sulfur; or $R^{12A}$, when $R^{11A}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12A}$, when a substituent on nitrogen, is:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, or $C_1$–$C_4$ haloalkyl;

$R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_3$–$C_6$ alkoxyalkyl substituted with 0–3 $R^{11A}$;
an amine protecting group when $R^{13}$ is bonded to N or a hydroxy protecting group when $R^{13}$ is bonded to O;

$R^{14}$ is selected from: hydrogen; hydroxy; $C_1$–$C_6$ alkoxy; $C_2$–$C_6$ alkenyl; phenyl; benzyl; an amine protecting group when $R^{14}$ is bonded to N; a hydroxy protecting group when $R^{14}$ is bonded to O; or $C_1$–$C_6$ alkyl substituted with 0–3 groups selected from OH, $C_1$–$C_4$ alkoxy, halogen, $NH_2$, or —$NH(C_1$–$C_4$ alkyl);

$R^{13}$ and $R^{14}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{13A}$ and $R^{14A}$ are independently selected from: H or $C_1$–$C_6$ alkyl;

$R^{13A}$ and $R^{14A}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{15}$ is H or $CH_3$;
m is 0, 1 or 2;

said process comprising the following steps:
(1) (a) contacting a compound of formula (I):

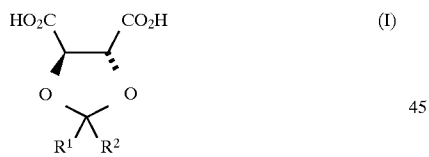

in an aprotic solvent with a carboxyl activating agent, followed by; (b) addition of a N,O-dialkylhydroxylamine of formula $R^6NHOR^5$, to form a compound of formula (II):

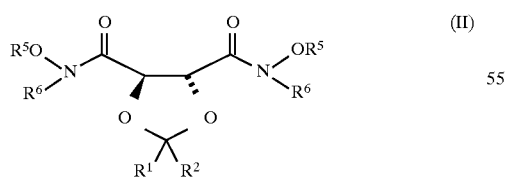

wherein $R^1$ and $R^2$ are defined as above and $R^5$ and $R^6$ are independently $C_1$–$C_4$ alkyl or benzyl;

(2) contacting a compound of formula (II) in an aprotic solvent with a nucleophilic organometallic reagent, said nucleophilic organometallic reagent being suitable for the addition of a $R^4$- or $R^7$-substituent to amides of the structure of compound (II), to form a compound of formula (III):

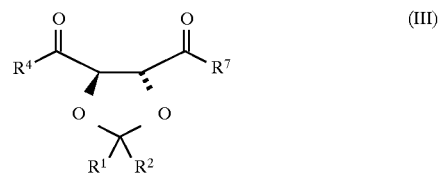

wherein $R^1$, $R^2$, $R^4$ and $R^7$ are defined as above ;

(3) reacting a compound of formula (III) in a protic solvent with a hydroxylamine of formula $NH_2OR^3$, to form a compound of formula (IV):

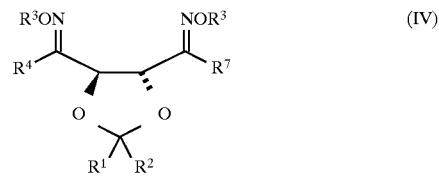

wherein $R^1$, $R^2$, $R^4$ and $R^7$ are defined as above and $R^3$ is hydrogen, $C_1$–$C_6$ alkyl, benzyl, arylcarbonyl or ($C_1$–$C_6$ alkyl)carbonyl.

11. A process for the preparation of compounds of formula (III):

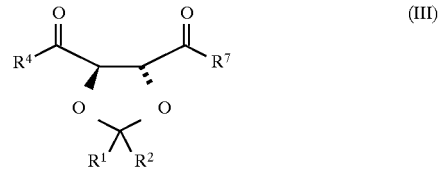

wherein:
$R^1$ and $R^2$ are independently: H, $C_1$–$C_4$ alkyl, $C_1$–$C_4$ alkoxy, $C_6$–$C_{10}$ aryl, $C_7$–$C_{14}$ arylalkyl, $C_1$–$C_4$ haloalkyl, $C_3$–$C_7$ cycloalkyl, or taken together to form keto;

alternatively, $R^1$ and $R^2$ are taken together with the carbon to which they are attached to form a 3–7 membered saturated carbocyclic ring system;

$R^3$ is hydrogen, $C_1$–$C_6$ alkyl, benzyl, arylcarbonyl or ($C_1$–$C_6$ alkyl) carbonyl;

$R^4$ and $R^7$ are independently:
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_4$ carbocyclic ring system substituted with 0–3 $R^{11}$ or 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;

$R^{11}$ is selected from one or more of the following:
H, keto, halogen, cyano, —$CH_2NR^{13}R^{14}$, —$NR^{13}R^{14}$, —$OR^{13}$, $C_1$–$C_4$ alkyl, $C_2$–$C_4$ alkenyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino) ethoxy, azido;
$C_3$–$C_{10}$ cycloalkyl substituted with 0–2 $R^{12}$;
$C_1$–$C_4$ alkyl substituted with 0–2 $R^{12}$;
aryl($C_1$–$C_3$ alkyl)-, substituted with 0–2 $R^{12}$;
$C_2$–$C_6$ alkoxyalkyl-, substituted with 0–2 $R^{12}$;
a $C_5$–$C_{14}$ carbocyclic residue substituted with 0–3 $R^{12}$; or a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is:

H, halogen, cyano, —$CH_2N(R^{13A})R(^{14A})$, $N(R^{13A})R(^{14A})$, —OH, $C_2$–$C_6$ alkoxyalkyl, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, azido, aryl($C_1$–$C_3$ alkyl), a $C_5$–$C_{14}$ carbocyclic residue; or a 5- to 10-membered heterocyclic ring system containing 1 to 4 heteroatoms independently selected from oxygen, nitrogen or sulfur, said heterocyclic ring system substituted with 0–3 $R^{12A}$;

$R^{12}$, when a substituent on carbon, is:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkylene, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or a 5- or 6-membered heterocyclic ring containing from 1 to 4 heteroatoms independently selected from oxygen, nitrogen or sulfur; or $R^{12}$, when $R^{11}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12}$, when a substituent on nitrogen, is:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, or $C_1$–$C_4$ haloalkyl;

$R^{12A}$, when a substituent on carbon, is:

phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, $C_3$–$C_6$ cycloalkoxy, —$OR^{13a}$, $C_1$–$C_4$ alkyl substituted with —$NH_2$, —$NH_2$, —NHMe, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, 2-(4-morpholino)ethoxy, or a 5- or 6-membered heterocyclic ring containing from 1 to 4 heteroatoms independently selected from oxygen, nitrogen or sulfur; or $R^{12A}$, when $R^{11A}$ is a 5- to 10-membered heterocyclic ring system, may be a 3- or 4-carbon chain attached to adjacent carbons on the 5- to 10-membered heterocyclic ring to form a fused 5- or 6-membered ring, the fused 5- or 6-membered ring being optionally substituted on the 3- or 4-carbon chain with halogen, $C_1$–$C_4$ alkyl, $C_1$–$C_4$ alkoxy, hydroxy, or —$NR^{13}R^{14}$;

$R^{12A}$, when a substituent on nitrogen, is:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NH_2$, —$NH_2$, $C_2$–$C_6$ alkoxyalkyl, or $C_1$–$C_4$ haloalkyl;

$R^{13}$ is selected from:

H;

phenyl substituted with 0–3 $R^{11A}$;

benzyl substituted with 0–3 $R^{11A}$;

$C_1$–$C_6$ alkyl substituted with 0–3 $R^{11A}$;

$C_2$–$C_4$ alkenyl substituted with 0–3 $R^{11A}$;

$C_3$–$C_6$ alkoxyalkyl substituted with 0–3 $R^{11A}$;

an amine protecting group when $R^{13}$ is bonded to N; or a hydroxy protecting group when $R^{13}$ is bonded to O;

$R^{14}$ is selected from: hydrogen; hydroxy; $C_1$–$C_6$ alkoxy; $C_2$–$C_6$ alkenyl; phenyl; benzyl; an amine protecting group when $R^{14}$ is bonded to N; a hydroxy protecting group when $R^{14}$ is bonded to O; or $C_1$–$C_6$ alkyl substituted with 0–3 groups selected from OH, $C_1$–$C_4$ alkoxy, halogen, $NH_2$, or —$NH(C_1$–$C_4$ alkyl);

$R^{13}$ and $R^{14}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{13A}$ and $R^{14A}$ are independently selected from: H or $C_1$–$C_6$ alkyl;

$R^{13A}$ and $R^{14A}$ alternatively join to form —$(CH_2)_4$-, —$(CH_2)_5$-, —$CH_2CH_2N(R^{15})CH_2CH_2$—, or —$CH_2CH_2OCH_2CH_2$—;

$R^{15}$ is H or $CH_3$;

m is 0, 1 or 2;

said process comprising the following steps:

(1) (a) contacting a compound of formula (I):

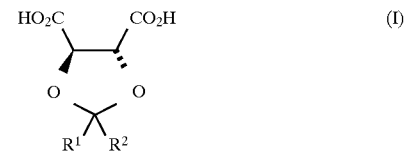

in an aprotic solvent with a carboxyl activating agent, followed by; (b) addition of a N,O-dialkylhydroxylamine of formula $R^6NHOR^5$, to form a compound of formula (II):

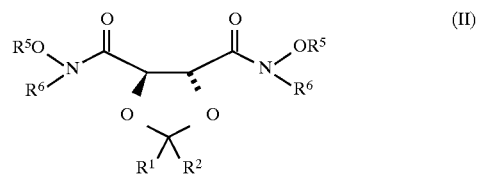

wherein $R^1$ and $R^2$ are defined as above and $R^5$ and $R^6$ are independently $C_1$–$C_4$ alkyl or benzyl;

(2) contacting a compound of formula (II) in an aprotic solvent with a nucleophilic organometallic reagent, said nucleophilic organometallic reagent being suitable for the addition of a $R^4$- or $R^7$-substituent to amides of the structure of compound (II), to form a compound of formula (III).

12. A process of claims 9–11 wherein:

$R^1$ and $R^2$ are methyl, ethyl, or taken together with the carbon to which they are attached to form cyclopentyl;

$R^4$ and $R^7$ are $C_1$–$C_8$ alkyl substituted with 0–1 $R^{11}$;

$R^{11}$ is

H; halogen; —$OR^{13}$;

$C_3$–$C_{10}$ cycloalkyl substituted with 0–2 $R^{12}$;

aryl substituted with 0–2 $R^{12}$; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, or oxazolidinyl, said heterocyclic ring system being substituted with 0–2 $R^{12}$;

$R^{12}$, when a substituent on carbon, is selected from one or more of the following:

benzyloxy, halogen, methyl, $C_1$–$C_4$ alkoxy, $CF_3$, 2-(4-morpholino)ethoxy, cyano, $C_3$–$C_6$ cycloalkoxy, $C_1$–$C_4$ alkyl substituted with —$NR^{13}R^{14}$, or —$NR^{13}R^{14}$;

$R^{12}$, when a substituent on nitrogen, is methyl;

$R^{13}$ is H, $C_1$–$C_4$ alkyl, $C_2$–$C_4$ alkenyl, or benzyl;

$R^{14}$ is H, $CF_3$, $C_1$–$C_4$ alkyl, $C_1$–$C_4$ alkoxy, $C_2$–$C_4$ alkenyl, or benzyl;

$R^{13}$ and $R^{14}$ alternatively join to form —$(CH_2)_4$-, —$(CH_2)_5$-, —$CH_2CH_2N(R^{15})CH_2CH_2$— or —$CH_2CH_2OCH_2CH_2$—.

13. A process as in one of claims 9–11, wherein:

$R^1$ and $R^2$ are methyl;

$R^4$ and $R^7$ are benzyl, fluorobenzyl, pyrrolylmethyl, methoxybenzyl, isobutyl, n-octyl, n-hexyl, dimethylaminobenzyl, thienylmethyl, pyridylmethyl, or napthylmethyl.

14. A process of claim 9 wherein one or more of the following conditions is met:

the carboxyl activating agent in step (1) is: 1,1'-carbonyldiimidazole, thionyl chloride, oxalyl chloride, isobutylchloroformate, or 1-(3-dimethylaminopropyl)-3-ethylcarbodiimide hydrochloride;

the N,O-dialkylhydroxylamine in step (1) is N,O-dimethylhydroxylamine hydrochloride;

the aprotic solvent in step (1) is: methylene chloride, tetrahydrofuran, N,N-dimethylformamide, or dimethoxyethane;

the organometallic reagent in step (2) is an organolithium or organomagnesium halide reagent;

the aprotic solvent in step (2) is: tetrahydofuran, ether, or hexane;

the hydroxylamine of step (3) is an hydroxylamine hydrochloride;

the reaction of step (3) is carried out in the absence of a base;

the reducing agent of step (4) is: lithium aluminum hydride, borane, diisobutoxyaluminum hydride, or catalytic hydrogenation in the presence of a Raney nickel catalyst.

* * * * *